United States Patent
Wu et al.

(10) Patent No.: US 10,688,078 B2
(45) Date of Patent: Jun. 23, 2020

(54) METHOD FOR TREATING AN ALLERGIC DISEASE

(71) Applicant: Arjil Biotech Holding Company Limited, Hsinchu (TW)

(72) Inventors: Yeh B Wu, Taipei (TW); Jir-Mehng Lo, Hsinchu County (TW); Hui Ju Liang, Taipei (TW); Pei-Hsin Lin, Hsinchu County (TW)

(73) Assignee: ARJIL BIOTECH HOLDING COMPANY LIMITED, Hsinchu (TW)

( * ) Notice: Subject to any disclaimer, the term of this patent is extended or adjusted under 35 U.S.C. 154(b) by 0 days.

(21) Appl. No.: 16/504,595

(22) Filed: Jul. 8, 2019

(65) Prior Publication Data

US 2020/0009110 A1 Jan. 9, 2020

Related U.S. Application Data

(60) Provisional application No. 62/694,779, filed on Jul. 6, 2018.

(51) Int. Cl.

| | | |
|---|---|---|
| *A61K 31/22* | (2006.01) | |
| *A61K 31/34* | (2006.01) | |
| *A61K 31/122* | (2006.01) | |
| *A61K 31/365* | (2006.01) | |
| *A61K 31/222* | (2006.01) | |
| *A61P 1/16* | (2006.01) | |
| *A61K 36/9062* | (2006.01) | |
| *A61K 36/9068* | (2006.01) | |
| *A61P 17/06* | (2006.01) | |
| *A61K 36/53* | (2006.01) | |

(52) U.S. Cl.
CPC .......... *A61K 31/365* (2013.01); *A61K 31/122* (2013.01); *A61K 31/222* (2013.01); *A61K 36/53* (2013.01); *A61K 36/9062* (2013.01); *A61K 36/9068* (2013.01); *A61P 1/16* (2018.01); *A61P 17/06* (2018.01)

(58) Field of Classification Search
CPC ....... A61K 31/22; A61K 31/34; A61K 31/122
USPC ......................................... 514/468, 546, 690
See application file for complete search history.

(56) References Cited

U.S. PATENT DOCUMENTS

| | | | |
|---|---|---|---|
| 7,252,845 B2 | 8/2007 | Weidner et al. | |
| 7,588,788 B2 * | 9/2009 | Chaung | A61K 36/9068 424/725 |
| 9,801,918 B2 * | 10/2017 | Joshi | A61K 31/365 |
| 2016/0022756 A1 * | 1/2016 | Jakobsen | A61K 31/225 424/756 |

OTHER PUBLICATIONS

International Search Report for Appl. No. PCT/US19/40780 dated Oct. 17, 2019.
Seo, J.W., et al, "1'-Acetoxychavicol Acetate Isolated fron Alpinia galanga Ameliorates Ovalbumin-Induced Asthma in Mice," PLOS ONE, Feb. 2013, vol. 8, No. 2, pp. 1-8.
Tzeng, T.F., et al, "Zerumbone, a Natural Cyclic Sesquiterpene of Zingiber zerumbet Smith, Attenuates Nonalcoholic Fatty Liver Disease in Hamsters Fed on High-Fat Diet," Evidence-Based Complementary and Alternative Medicine, Aug. 23, 2019, vol. 2013, pp. 1-9.
Written Opinion of the International Searching Authority for Appl. No. PCT/US19/40780 dated Oct. 17, 2019.

* cited by examiner

*Primary Examiner* — Raymond J Henley, III
(74) *Attorney, Agent, or Firm* — Birch, Stewart, Kolasch & Birch, LLP

(57) ABSTRACT

The invention relates to a use of a compound for manufacturing a medicament for treating an allergic disease, wherein the compound is selected from the group consisting of ovatodiolide, 1'-acetoxychavicol acetate, zerumbone and combination thereof. Also provided is a method and a composition for treating an allergic disease.

10 Claims, 15 Drawing Sheets

1. Naïve
2. IMQ/Base
3. IMQ/AR100
4. IMQ/AR111
5. IMQ/AR112

METHOD FOR TREATING AN ALLERGIC DISEASE

CROSS REFERENCE TO RELATED APPLICATION

This non-provisional application claims the benefit under 35 U.S.C. § 119(e) to U.S. Provisional Application No. 62/694,779, filed on Jul. 6, 2018, which is hereby expressly incorporated by reference into the present application.

FIELD OF THE INVENTION

The invention relates to a method for treating an allergic disease. In particular, the invention relates to a composition for treating an allergic disease.

BACKGROUND OF THE INVENTION

Allergies are due to immune system disorders of the body, which reacts excessively to allergens in the environment. Allergens entering the body and IgE antibodies will be combined to stimulate mast cells to release substances like histamine, whereby the inflammatory response are generated in body tissues, resulting in chronic inflammation of skin, mucosal tissues or blood vessels. In recent years, it has gradually become a major threat to our health. Allergies are related to the second type of helper T cells (Th2) among B cells and T cells. The characteristic reactions of Th2 cells are the generation of inerleukin-4, IL-4, and IL-5. IL-4 helps B cells to produce sensitization antibodies of immunoglobulin E. IL-5 can attract eosinophilic white blood cells, which will release some of the inflammatory mediators, resulting in much severe allergic symptoms. The first type of T helper cells is responsible for the immunity of cells, which can inhibit the Th2 response by the secretion of cytokines, such as the secretion of interferons: IFN-γ, IgG2a, IL-2, IL-3 and so on.

BRIEF SUMMARY OF THE INVENTION

The invention unexpectedly finds some compounds have anti-allergic effect.

Accordingly, in one aspect, the invention provides a method for treating an allergic disease which comprises administering to a subject in need thereof a therapeutically effective amount of a compound selected from the group consisting of ovatodiolide, 1'-acetoxychavicol acetate, zerumbone and combination thereof.

In another aspect, the invention provides a use of a compound in manufacturing a medicament for treating an allergic disease, wherein the compound is selected from the group consisting of ovatodiolide, 1'-acetoxychavicol acetate, zerumbone and combination thereof.

In a further aspect, the invention also provides a pharmaceutical composition for treating an allergic disease comprising a therapeutically effective amount of a compound selected from the group consisting of ovatodiolide, 1'-acetoxychavicol acetate, zerumbone and combination thereof.

In a yet aspect, the invention provides a healthcare composition for alleviating an pain caused by an allergic disease comprising a therapeutically amount of a compound selected from the group consisting of ovatodiolide, 1'-acetoxychavicol acetate, zerumbone and combination thereof.

In one embodiment of the invention, the compound may be provided from a plant or an herb. For example, ovatodiolide and/or zerumbone may be provided from a plant, *Anisomeles indica*; 1'-Acetoxychavicol acetate from *Alpinia galangal*, and zerumbone from *Zingiber zerumbet*.

In a further yet aspect, the invention provides an herbal composition or a pharmaceutical composition comprising an extract from an herb selected from the group consisting of *Anisomeles indica, Alpinia galangal, Zingiber zerumbet* and combination thereof.

According to an embodiment of the invention, the allergic disease is a condition caused by hypersensitivity of the immune system to typically harmless substances in the environment, which may be selected from the group consisting of hay fever, food allergies, atopic dermatitis, asthma, psoriasis, anaphylaxis psoriasis, atopic dermatitis, contact dermatitis or eczema, autoimmune disease, osteoarthritis, allergy rhinitis, seborrheic dermatitis, psoriasis arthritis and poison ivy.

Particularly, the autoimmune disease is selected from the group consisting of autoimmune hepatitis, autoimmune pancreatitis, Sjogren' syndrome, ulcerative colitis, Crohn's disease, reflex sympathetic dystrophy, post myocardial infarction syndrome, rheumatoid rhinitis, multiple sclerosis, and cardiomyopathy. In one embodiment of the invention, the autoimmune disease is autoimmune hepatitis.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1:
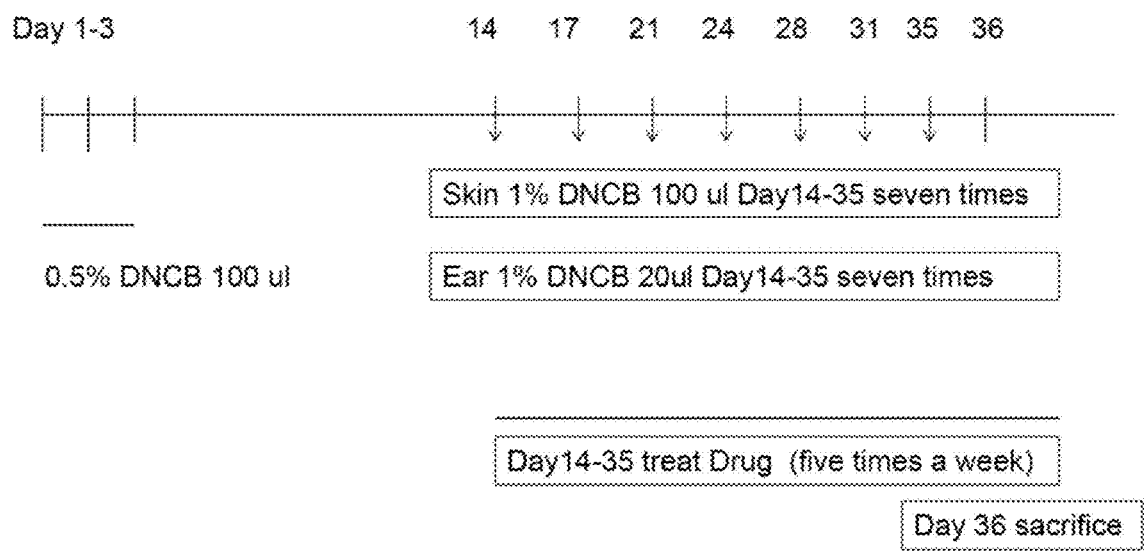
FIG. 1 is a schematic diagram for inducing contact dermatitis in an animal.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The invention provides a method for treating an allergic disease which comprises administering to a subject in need thereof a therapeutically effective amount of a compound selected from the group consisting of ovatodiolide, 1'-acetoxychavicol acetate, zerumbone and combination thereof.

In the invention, ovatodiolide, also called as "AR001DS1" herein, may be isolated and purified from Anisomeles indica, which has the structure of

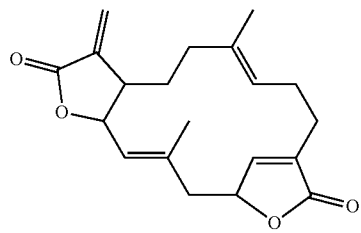 [SMILES: C=C1C(=O)OC2/C=C(\C)CC3C=C(CC/C=C(\C)CCC12)C(=O)O3]

In the invention, 1'-acetoxychavicol acetate, also called as "AR001DS2" herein, may be isolated and purified from Alpinia galanga, which has the structure of

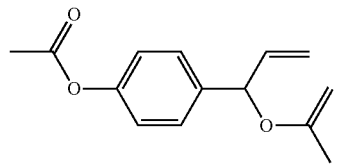 [SMILES: C=CC(OC(=C)C)c1ccc(OC(C)=O)cc1]

In the invention, zerumbone, also called as "AR001DS3" herein, be isolated and purified from Zingiber zerumbet, which has the structure of

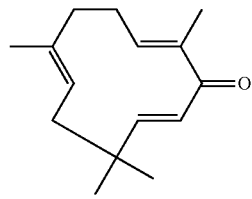 [SMILES: C/C1=C\CC(C)(C)/C=C/C(=O)/C(C)=C/CC1]

The invention provides a use of a compound in manufacturing a medicament for treating an allergic disease, wherein the compound is selected from the group consisting of ovatodiolide, 1'-acetoxychavicol acetate, zerumbone and combination thereof.

The invention also provides a healthcare or pharmaceutical composition for treating an allergic disease comprising a therapeutically effective amount of a compound selected from the group consisting of ovatodiolide, 1'-acetoxychavicol acetate, zerumbone and combination thereof.

Since the compound may be provided from a plant or an herb. For example, ovatodiolide and/or zerumbone may be provided from a plant, Anisomeles indica; 1'-acetoxychavicol acetate from Alpinia galangal, and zerumbone from Zingiber zerumbet. Accordingly, the invention provides an herbal composition or a pharmaceutical composition comprising an extract from an herb selected from the group consisting of Anisomeles indica, Alpinia galangal, Zingiber zerumbet and combination thereof.

As used herein, the term "an allergic disease" refers to a condition caused by hypersensitivity of the immune system to typically harmless substances in the environment, including particularly an autoimmune disease. In the embodiments of the invention, the allergic disease is selected from the group consisting of hay fever, food allergies, atopic dermatitis, asthma, psoriasis, anaphylaxis psoriasis, atopic dermatitis, contact dermatitis or eczema, seborrheic dermatitis, psoriasis arthritis, poison ivy, rheumatoid rhinitis, multiple sclerosis, osteoarthritis, allergy rhinitis and cardiomyopathy. The symptoms may include red eyes, an itchy rash, sneezing, a runny nose, shortness of breath, or swelling. In the examples of the invention, the allergic disease is allergic dermatitis, in particular, atopic eczema or psoriasis.

As used herein, the term "autoimmune disease" refers to a condition arising from an abnormal immune response to a normal body part. There are at least 80 types of autoimmune diseases. Examples of autoimmune diseases include, but not limited to, autoimmune hepatitis, autoimmune pancreatitis, celiac disease, diabetes mellitus type 1, Sjogren' syndrome, ulcerative colitis, Crohn's disease, reflex sympathetic dystrophy, post myocardial infarction syndrome, Graves' disease, inflammatory bowel disease, multiple sclerosis, psoriasis, rheumatoid arthritis, cardiomyopathy and systemic lupus erythematosus.

According to the invention, the extract of *Anisomeles indica* may be prepared by the following process: extracting *Anisomeles indica* with an ethanol to obtain a crude extract, loading the crude extract to a silica-filled chromatographic column, and subjecting to a gradient elution with the eluents: n-hexane/ethyl acetate, hexane/ethyl acetate/methanol and methanol, to obtain a fraction; separating the fraction by using a silica-filled chromatographic column, and subjecting to a gradient elution with the eluents: dichloromethane, dichloromethane/methanol and methanol, to obtain a concentrate; and recrystallizing the concentrate with n-hexane/ethyl acetate to obtain a crystallite. Ovatodiolide and/or zerumbone may be provided from a plant, *Anisomeles indica*.

According to the invention, the extract of *Alpinia galangal* may be prepared by the following process: extracting *Alpinia galangal* with cyclohexane to obtain a crude extract, loading the crude extract to a silica-filled chromatographic column, and subjecting to a gradient elution with the eluents: n-hexane/ethyl acetate, n-hexane/ethyl acetate/methanol and methanol to obtain an isolate; and recrystallizing the isolate with n-hexane/ethyl acetate to obtain a crystallite. 1'-Acetoxychavicol acetate may be extracted from *Alpinia galangal*.

The term "subject" as used herein includes human or non-human animals, such as companion animals (e.g. dogs, cats, etc.), farm animals (e.g. cattle, sheep, pigs, horses, etc.), or experimental animals (e.g. rats, mice, guinea pigs, etc.).

The term "treating" used herein refers to administrating one or more active agents to a subject in need thereof who has an allergic disease, symptoms of an allergic disease, or being subject an allergic disease. The object of which is to heal, treat, alleviate, reduce, alter, correct, improve, or affect the disease, the symptoms of the disease, or being subject to the disease.

The term "therapeutically effective amount" as used herein refers to an amount of a compound or pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

For use in therapy, the therapeutically effective amount of the composition is formulated as a pharmaceutical composition for administration. Accordingly, the invention provides a pharmaceutical composition comprising a therapeutically effective amount of the active ingredient(s) and one or more pharmaceutically acceptable carriers.

The term "pharmaceutically acceptable carriers" used herein refers to a carrier(s), diluent(s) or excipient(s) that is acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

According to the present invention, the form of the pharmaceutical composition may be tablets, pills, powder, lozenges, packets, troches, elixers, suspensions, ointments, lotions, solutions, syrups, soft and hard gelatin capsules, suppositories, sterilized injection fluid, and packaged powder. In one particular example of the invention, the pharmaceutical composition is formulated in the form of ointment. Such formulations may be prepared by any method known in the art of pharmacy.

According to the invention, the pharmaceutical composition may be adapted for administration by any appropriate route, including but not limited to oral, rectal, nasal, topical, vaginal, or parenteral route. In one particular example of the invention, the pharmaceutical composition is formulated for topical administration. Such formulations may be prepared by any method known in the art of pharmacy.

According to the invention, the method, use or composition described herein could be administrated a subject in combination with at least one additional allergy medications. Exemplified allergy medications which are responsive include, without limitation, ketorolac tromethamine, pemirolast potassium, ketotifen, loratadine, neodocromil sodium, fexofenadine, loteprednol etabonate, azelastine, ipratropium bromide, epinephrine, beclomethasone, diphenhydramine, desloratadine, loratadine, dexamethasone, epinastine, fluticasone.

The present invention is further illustrated by the following examples, which should be construed as illustrative only and not in any way limit the remainder of the present invention. Without further illustration, it is believed that those skilled in the art will be able to make the best use of the present invention based on the description herein.

PREPARATION EXAMPLES

1. Contact Dermatitis Animal Experiment
Contact Dermatitis Animal Model:
After 7 to 8 weeks from the birth of BALB/c mice, back shaving was conducted, and the allergy drug, 1-chloro-2,4-dinitrobenzene (DNCB), was used as a stimulant to induce the symptoms of contact dermatitis, such as atopic eczema. As shown in FIG. 1, the back was smeared with 100 μl of 0.5% DNCB on Day 1-3; the skins were challenged with 100 μl of 1% DNCB and the ears were challenged with 20 μl of 1% DNCB on Day 14. The smearing could also be conducted on Days 17, 21, 24, 28, 31, and 35. On the other hand, from Day 14, the test ointments were applied five times a week for three weeks. On Day 36, the mice were sacrificed.

Mice Grouping:
Mice were divided into five groups and each group had four mice. The names, drugs, and ointments are shown in Table 1:

TABLE 1

| Group (short title) | Agent for inducing atopic eczema | Treatment (in an ointment) | Remark |
|---|---|---|---|
| 1 Normal group (N) | acetone and olive oil | acetone and olive oil | Non-induced atopic eczema without treatment |
| 2 Sensitization group (S) | DNCB in acetone and olive oil | acetone and olive oil | Induced atopic eczema without treatment |

TABLE 1-continued

| | Group (short title) | Agent for inducing atopic eczema | Treatment (in an ointment) | Remark |
|---|---|---|---|---|
| 3 | Ointment blank group (SV) | DNCB in acetone and olive oil | blank ointment in acetone and olive oil | Induced atopic eczema with treatment |
| 4 | A100 | DNCB was dissolved in acetone and olive oil | The ointment containing AR001DS1 and AR001DS2 was dissolved in acetone and olive oil | Induced atopic eczema with treatment |
| 5 | V2 | DNCB was dissolved in acetone and olive oil | The ointment containing AR001DS1 and AR001DS3 was dissolved in acetone and olive oil | Induced atopic eczema with treatment |

The mice were treated with the composition of ovatodiolide (AR001DS1) and 1'-acetoxychavicol acetate (AR001DS2) added into the ointment, and the composition of ovatodiolide (AR001DS1) and zerumbone (AR001DS3) added into the ointment, called as the groups A100 and V2 respectively, wherein the amount of each compound is 2.5%.

Ear Swelling Measurement:

After the experiment, the thickness of the mice ears was measured and recorded.

Hematoxylin and Eosin (HE) Stain:

The skins and ears were taken off from the mice, fixed in the formalin and made into wax pieces. After sliced, they were stained with HE and the eosinophilic ball (eosinophil) infiltration and skin swelling results were observed.

ronment was kept at 25° C. Light and dark periods were in cycle every 12 hours. The mice were free to get adequate food and water.

Figure 2:
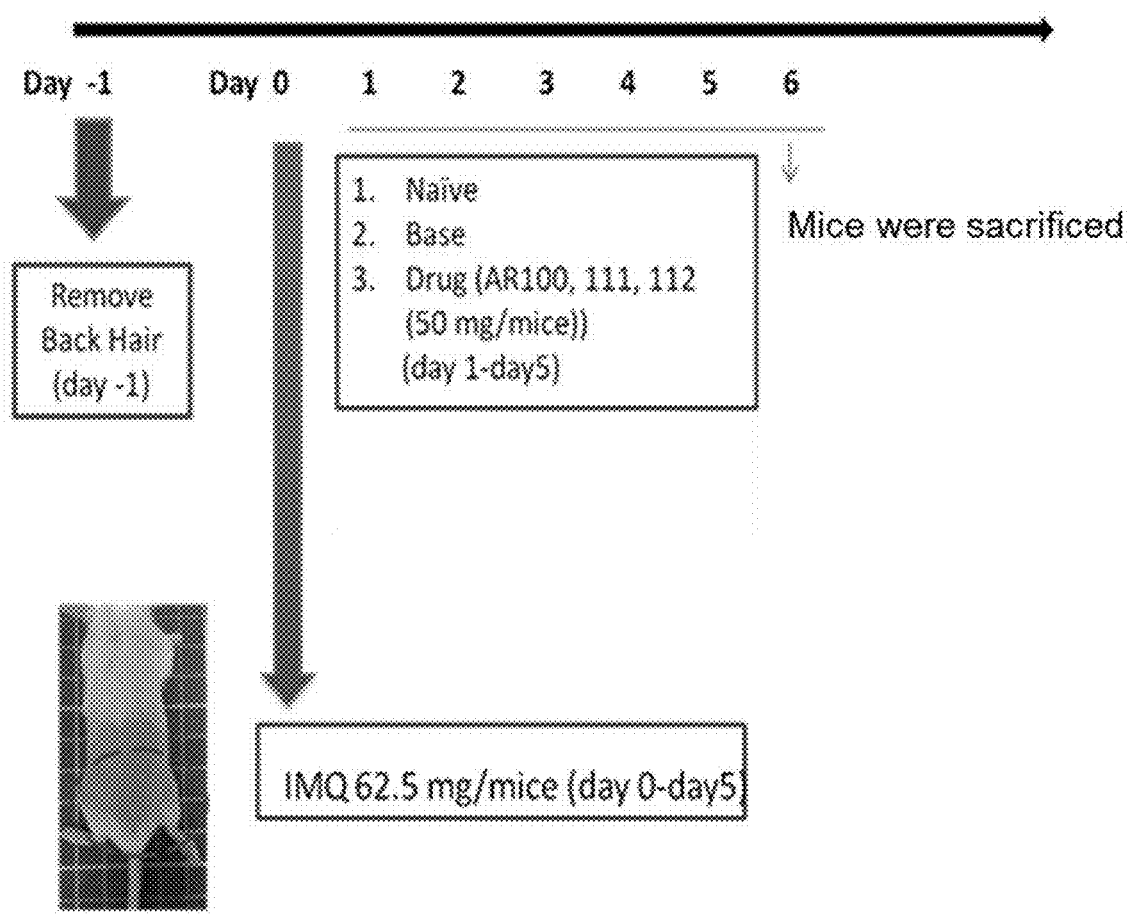
FIG. 2 is a schematic diagram for inducing psoriasis in an animal.

Psoriasis was induced by imiquimod (IMQ) in the mice. As shown in FIG. 2, on the day before the experiment, the mice were divided into two groups after the mice were depilated with shaving knives and depilatory creams.

The group treated with the composition of ovatodiolide (AR001DS1) and 1'-acetoxychavicol acetate (AR001DS2) was called as AR100; the group treated with ovatodiolide (AR001DS1) was called as AR111; and the group treated with the composition of ovatodiolide (AR001DS1) and zerumbone (AR001DS3) was called as AR112. Mice were divided into six groups and each group had eight mice. The names, drugs, and ointments are shown in Table 2:

TABLE 2

| | Group (short title) | Agent for inducing psoriasis | Treatment (in an ointment) | Remark |
|---|---|---|---|---|
| 1 | Normal group (N) | | acetone and olive oil | Non-induced psoriasis without treatment |
| 2 | Sensitization group (S, IMQ/ Base) | imiquimod (IMQ) | acetone and olive oil | Induced psoriasis without treatment |
| 3 | Ointment blank group (SV) | imiquimod (IMQ) | blank ointment in acetone and olive oil | Induced psoriasis with treatment |
| 4 | AR100 | imiquimod (IMQ) | The ointment containing AR001DS1 and AR001DS2 in acetone and olive oil | Induced psoriasis with treatment |
| 5 | AR111 | imiquimod (IMQ) | The ointment containing AR001DS1 was dissolved in acetone and olive oil | Induced psoriasis with treatment |
| 6 | AR112 | imiquimod (IMQ) | The ointment containing AR001DS1 and AR001DS3 was dissolved in acetone and olive oil | Induced psoriasis with treatment |

Skin Toluidine Blue Staining:

After the skins and ears of mice were fixed and sliced, they were stained with toluidine blue and the infiltration of mast cells were observed.

Analysis of Gene Expressions of Skins by the Real-Time Polymerase Chain Reaction (PCR):

A piece of skin was taken to extract its mRNA, and the gene expressions of IL-4 and IL-5 were analyzed by real-time PCR.

2. Psoriasis Animal Experiment

Psoriasis Animal Model:

The animals were 5-8 weeks old BALB/c mice from the National Laboratory Animal Center. The experimental envi- The mice of the Sensitization group (S, IMQ/Base) were smeared with 62.5 mg of IMQ on the backs of mice. After 4 hours, the mice were treated with 50 mg of AR100 (IMQ/AR100), 50 mg of AR111 (IMQ/AR111) or 50 mg of AR112 (IMQ/AR112). The drugs were smeared once a day for six days. The weights of mice were recorded and the mice were taken pictures every day. The redness and scaling conditions of the skins were observed and scored. On the last day of the experiment, the mice were sacrificed, and their skins were taken to conduct analyses on immunologic tissue staining and cytokines expressions.

3. Autoimmune Hepatitis Animal Experiment
Reagents

Concanavalin A (Con A) and dexamethasone (Dex) were purchased from Sigma-Aldrich (USA). ProcartaPlex™ Immunoassays kit was purchased from Corning Inc. (USA). GOP and GPT Fuji Dri-Chem slides were purchased from Winning Medical Inc. (Taiwan).

Animals

Male BALB/c mice (7-9 weeks old) were purchased from BioLASCO Taiwan Co., Ltd or National Laboratory Animal Center (NLAC, Taiwan). Animals were housed five per cage with food and water provided ad libitum throughout the experiments. Room temperature was maintained at 23±2° C. with an alternating 12 h light-dark cycle. Animals were acclimatized for one week to minimize the effect of stress before the experiments. All experimental protocols involving animals and their care were approved by the Institutional Animal Care and Use Committee (IACUC) in ITRI (ITRI-IACUC-2018-041 and ITRI-IACUC-2018-050; accredited by AAALAC) and were carried out according to the regulations of the Council of Agriculture, Taiwan.

Experimental Design and Hepatitis Induction

Con A was dissolved in pyrogen-free saline at a concentration of 3 mg/ml and intravenously injected at a dose of 15 mg/kg or 20 mg/kg of body weight to induce hepatitis. AR100DS1 and Dex were orally administered 30 min before and then 4 h and 8 h after Con A treatment. Blood and liver tissues were collected 24 h after Con A treatment. Serum were stored at −80° C. until analysis.

Analysis of Liver Enzymes

To assess the level of hepatocellular injury after Con A treatment, serum GPT and GOT levels were measured by Fuji Dri-Chem slides (Fuji, Japan).

Analysis of Serum Cytokines

The serum of the same group were pooled for cytokine assay. Cytokine levels were measured by ProcartaPlex™ Immunoassays kit according to manufacturer's instructions.

Histopathology

Liver tissues were fixed in 10% phosphate-buffered formaldehyde, embedded in paraffin, and stained with hematoxylin and eosin (H&E) in order to confirm tissue lesions. Tissue lesions were examined microscopically by a veterinary pathologist at BioLASCO Taiwan Co., Ltd. The criteria of severity grading system for all microscopic lesions were graded from 0 to 4 as follows: 0=none; 1=individual cell necrosis; 2=≤30% lobular necrosis; 3=≤60% lobular necrosis; 4=22 60% lobular necrosis.

Statistical Analysis

Data are presented as mean±SEM. In this study, Student's t-test was used to analyze the differences between drug- and vehicle-treated groups. The difference is regarded statistically significant when p value is less than 0.05.

4. Immune Responses of Mast Cells and Dendritic Cells
β-Hexosaminidase Secretion Assay RBL-2H3 cells were plated in a 24-well plate and then sensitized with anti-dinitrophenyl (DNP)-IgE overnight at 37° C. in a 5% $CO_2$ atmosphere. After washing, the cells were treated with AR001DS1 (12.5, 25, 50 and 100 μg/ml) at 37° C. for 30 min, and then stimulated with DNP-bovine serum albumin (BSA) at 37° C. for 30 min to induce degranulation. The supernatant was transferred to a 96-well microplate and incubated for 2 h with equal volume of 5 mM 4-nitrophenyl N-acetyl-b-glucosaminide in 0.1M citrate buffer (pH 4.5). The reaction was terminated by adding 200 ml of stop buffer (0.05M sodium carbonate, pH 10), and OD at 405 nm was determined using an ELISA plate reader.

ELISA Assay for TNF-α Secretion

DCs were isolated from C57BL/6 mice and incubated at 37° C. for 7 days. Then DCs were plated in a 24-well plate and cultured at 37° C. overnight in a 5% $CO_2$ atmosphere. DCs were treated with AR001DS1 (12.5, 25, 50 and 100 μg/ml) for 1 h, and then stimulated with lipopolysaccharide (LPS) for 4 h. The supernatants were collected and TNF-α secretion in culture supernatants was quantitated using an ELISA assay.

Example 1 Animal Experiment for Inducing Atopic Dermatitis

1. Appearance Observations and Analyses

The appearances of mice skins were photographed after mice were sacrificed at the end of the experiment. The mice of the normal group (N) had intact skins; the skins of the mice of the sensitization group (S) were rough and inflamed, and the ears of which were swelling. The remodeling phenomenon in skin was found after about 3-4 weeks from the stimulation of DNCB. In the group SV, the symptoms of the skin were not improved. However, it was found in each of the groups A100 and V2 the effects on improvement of atopic eczema, wherein the skin redness and skin swelling were significantly improved. In addition, at the process of breaking necks of mice, the group A100 and the group V2 were found to have no phenomenon in skin crack, wherein the fragile skin caused by atopic eczema was improved. Therefore, it was concluded that the symptoms caused by atopic eczema could be improved by the treatment of the composition of ovatodiolide and 1'-acetoxychavicol acetate (A100) and the composition of ovatodiolide and zerumbone (V2).

2. Ear Thickness Measurements and Analyses

Figure 3:
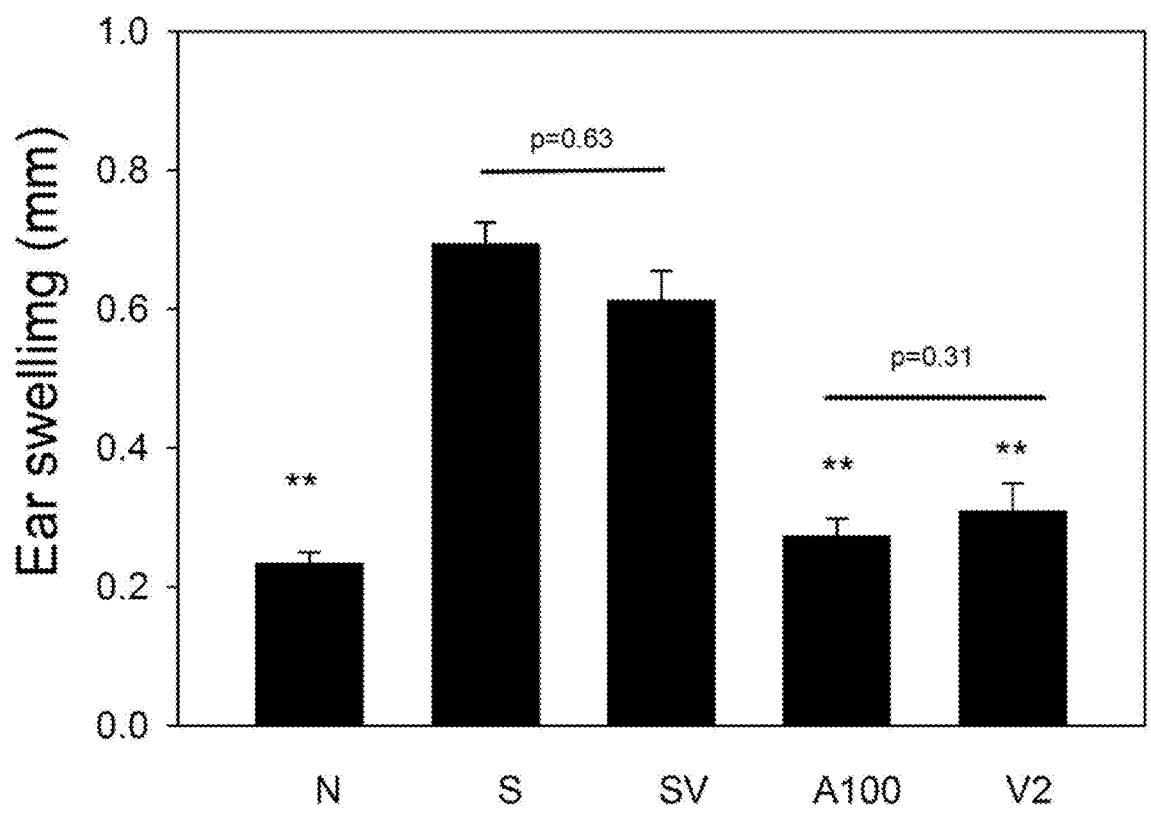
FIG. 3 provides the results of the ear swelling observation in the contact dermatitis animal experiments (**: $p<0.01$).

The thickness of the ears of the group SV was measured as 0.69±0.08 mm, which was significantly thicker than that of the normal group (N, 0.23±0.04 mm). As shown in FIG. 3, the ears of the groups A100 and V2 in thickness were measured as 0.27±0.07 mm (p<0.01) and 0.31±0.10 mm (p<0.001), respectively. It was found that the ear swelling of the groups A100 and V2 was significantly improved. The appearance of skins and the swelling of the ears were improved in both of the groups A100 and V2.

3. Observation and Analyses of Ear and Skin Slices

The ears and skins of the sacrificed mice were sliced and subjected to HE staining. It was found that the skins and ears of the sensitization group had the phenomenon of dermis layer thickening, many eosinophils were infiltrated in the skin tissues. On the other hand, in the groups A100 and V2, the swelling of the skins and the ears were reduced, the infiltration of eosinophils was decreased.

Specifically, eosinophils tended to accumulate in allergic parts such as the lungs of asthma and the skin parts of atopic dermatitis. This group of eosinophils gathered in the allergic parts will release more inflammatory substances, resulting in more severe inflammation on the infiltrated parts. Therefore, if the infiltration of eosinophils can be inhibited, there will be significant improvement on the symptoms of atopic dermatitis. It can be concluded that in the groups A100 and V2, the infiltration of eosinophils on skins and ears was significantly improved.

Figure 4:
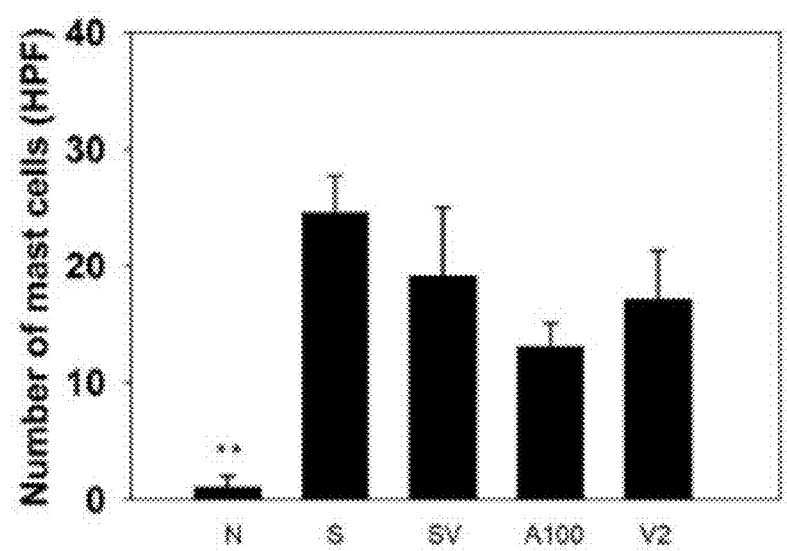
FIG. 4 provides the results of the ear biopsy of mast cell infiltration in the contact dermatitis animal experiment (**: $p<0.01$).
Figure 5:
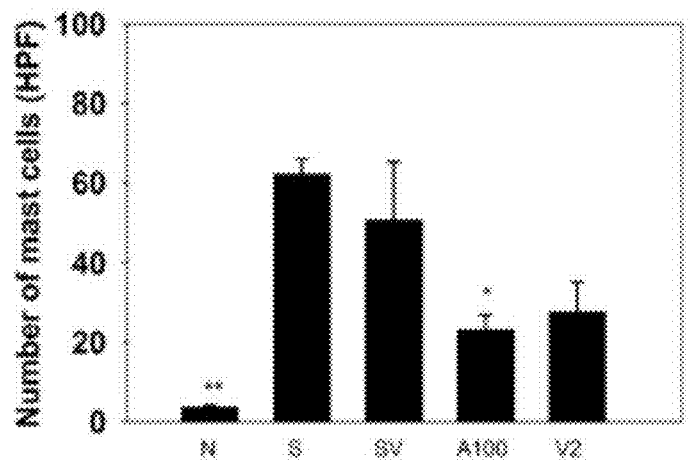
FIG. 5 provides the results of the skin biopsy of mast cell infiltration in the contact dermatitis animal experiment (*: $p<0.05$; **: $p<0.01$).

The skin and ear slices of the mice were also stained with toluidine blue and the mast cells were observed. The results are shown in FIG. 4 and FIG. 5. Mast cells are important immune cells for inducing allergic reactions. When IgE, allergens, and mast cells forming cross linking, the mast cells will be activated and induced to release histamine and leukotriene etc., resulting in allergic reactions on tissues. When a large number of activated mast cells are infiltrated in the affected area of the dermatitis, it will result in severe allergies and itching. In the experiment, it was found that there were many mast cell infiltrations in the skins or ears of the sensitized group (as shown in FIGS. 4 and 5), showing that the number of mast cells had a decreasing tendency as compared with the group S, having a great improvement on symptoms of skin allergies. Although the ear slices of the group A100 were not significantly different from the ear and skin slices of the group V2, the infiltration of mast cells was reduced.

4. Measurements of Antibodies in the Blood

Figure 6:
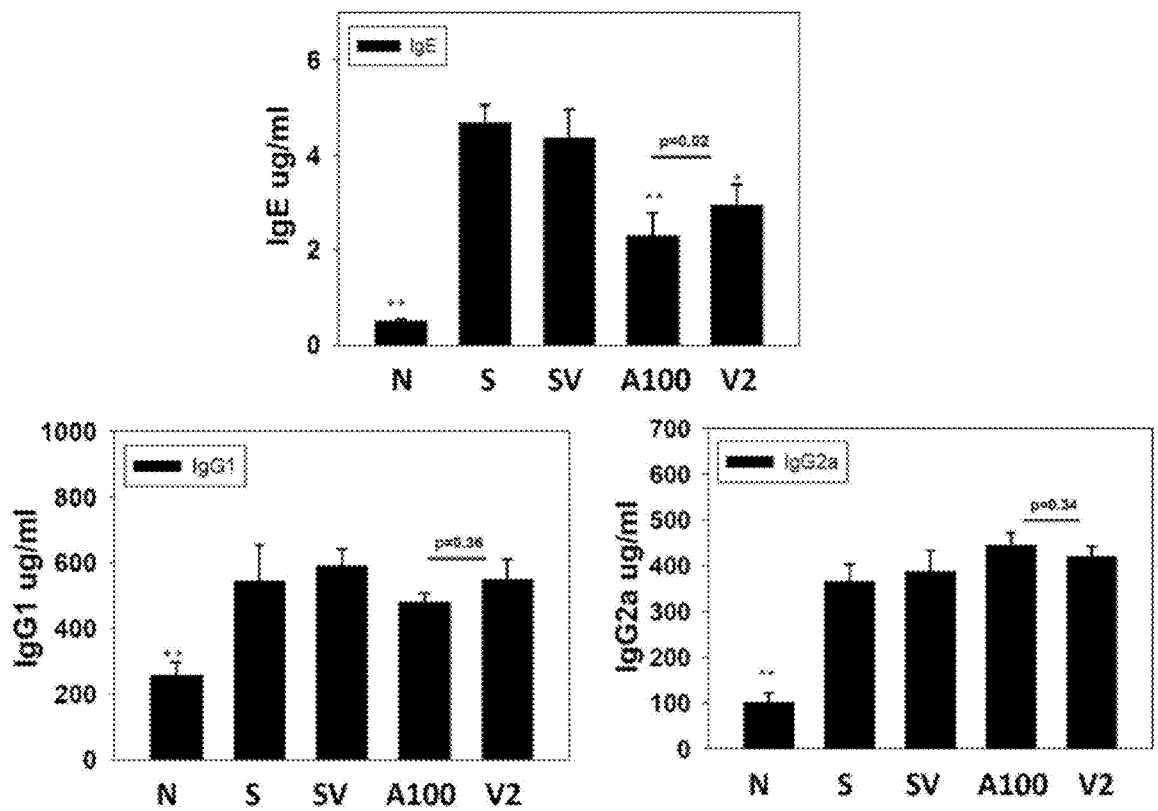
FIG. 6 provides the results of the contact dermatitis animal experiment (*: $p<0.05$; **: $p<0.01$).
Figure 7:
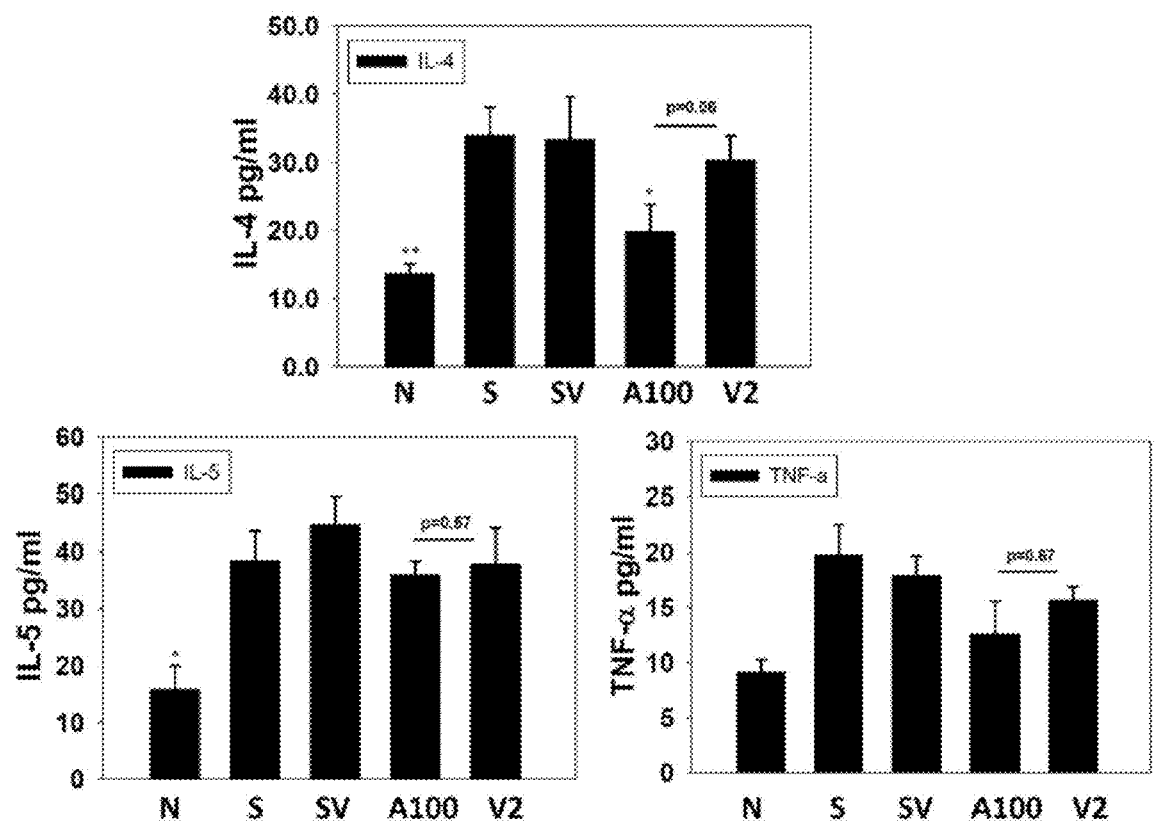
FIG. 7 is an analytical chart of serum cells reliance in an animal experiment for inducing a contact dermatitis in one embodiment of the invention (*: $p<0.05$; **: $p<0.01$).

As shown in FIGS. 6, 7 and 8, the generation of IgE was inhibited in the groups A100 and V2, while the inhibition to the generation of IgE in the group A100 is more than that in the group V2 (see FIG. 8). It could be concluded that the composition of ovatodiolide and 1'-acetoxychavicol acetate (A100) and the composition of ovatodiolide and zerumbone (V2) could inhibit the generation of IgE, showing a great improvement in skin allergies.

It was also found that the atopic dermatitis and the excessive activation of Th2 cells were closely related to each other. As shown in FIG. 7, the levels of IL-4, IL-5 and TNF-α of the group A100 were significantly different from that of the control group in reducing the IL-4 ($p<0.05$). As shown in FIG. 7, the composition containing AR001DS1 and AR001DS2 provided an effect on the levels of IL-5 and TNF-α, but showing a decreasing trend (see FIG. 7). In the group V2, the composition of AR001DS1 and AR001DS3 showed am effect in decreasing the levels of IL-4, IL-5 and TNF-α, but not significant.

As shown in FIG. 6, the composition containing AR001DS1 and AR001DS2 (the group AR100) had a tendency to inhibit IgG1 and promote IgG2a. As compared with the group AR100, the levels of IgG1 and the IgG2a in the blood in the group V2 were not significantly regulated.

Given the above, the composition of AR001DS1 and AR001DS2 provided an effect on the levels of IL-4 and IgE, which indirectly showed that the A100 could reduce the activity of Th2 cells. In the both groups A100 and V2, it could be found that the expression of TNF-α (the inflammatory marker) was reduced.

In summary, both the composition of AR001DS1 and AR001DS2 and the composition of AR001DS1 and AR001DS3 provide an effect on improvement of the symptoms of atopic dermatitis in mice. Although it is not particularly good for the role of reducing Th2 immune cells, but it was found that the levels of IgE and IL-4 in the blood were decreased in the group AR100, treated with the composition of AR001DS1 and AR002DS2. In the groups AR100 and/or V2, the infiltration of eosinophils and mast cells on the skin were found to be reduced, showing an improvement in skin swelling and inflammation.

Example 2 Psoriasis Animal Experiment

1. Appearance Observations and Analyses

The appearances of mice skins were observed and it was found that in the groups AR100 and AR112 the scaling and redness on the affected areas with psoriasis were effectively reduced, wherein the composition of AR0001DS1 and AR0002DS3 provided a significant effect on reduction in the symptoms of psoriasis.

2. Scores on Redness

Figure 8A:
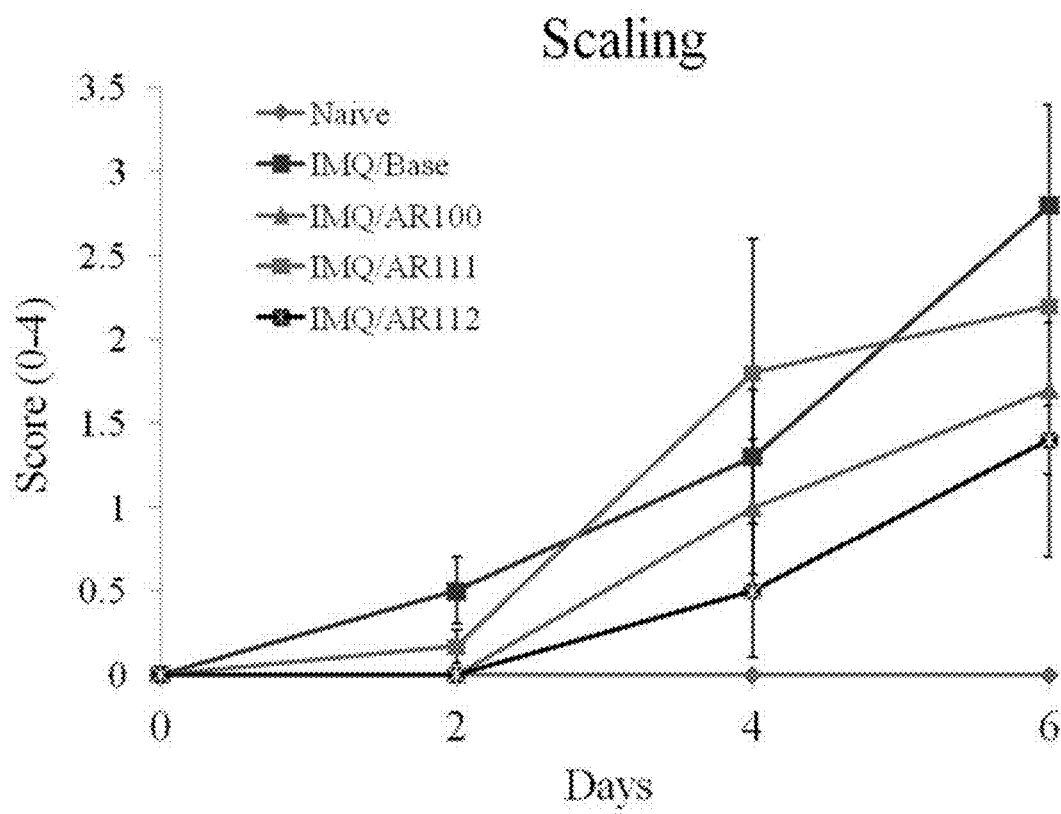
FIG. 8A is a chart showing the levels of desquamation in the psoriasis animal experiment.
Figure 8B:
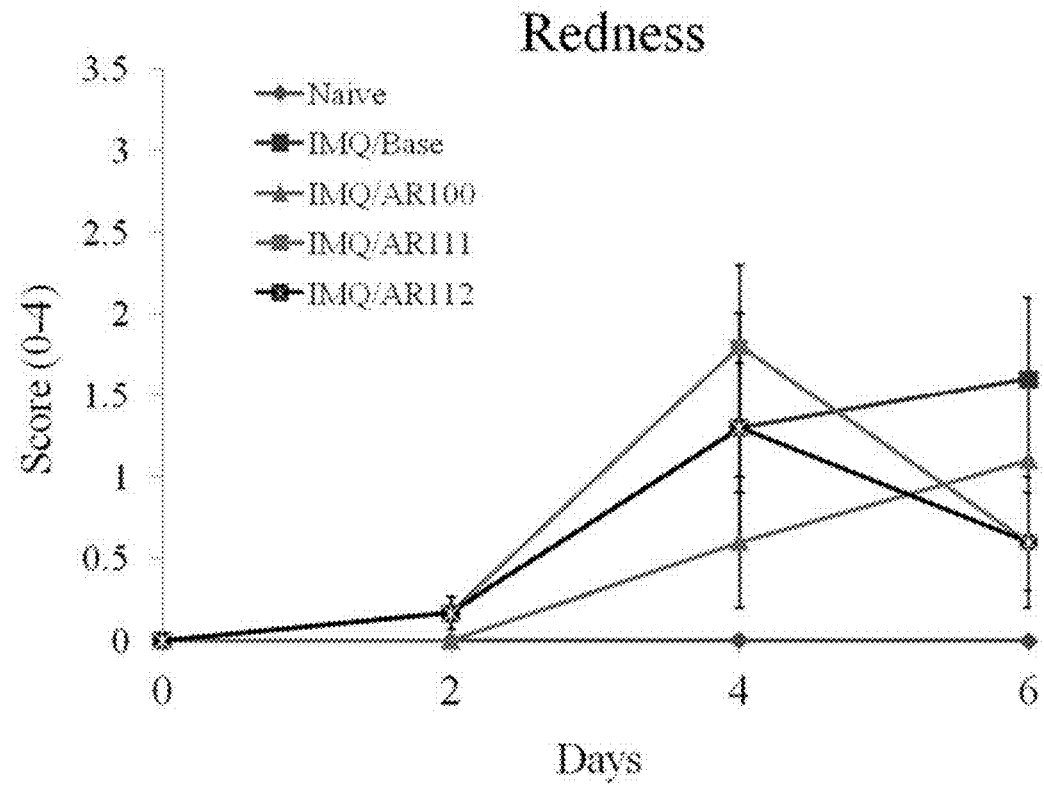
FIG. 8B is a chart showing the levels of redness of the psoriasis animal experiment.

The scale of redness was scored according to daily observation and recordation of the mice. The degree of skin scaling is shown in FIG. 8A, and the redness is shown in FIG. 8B. The data in FIGS. 8A and 8B were based on the Psoriasis Area and Severity Index (PAST), and the degrees of psoriasis scaling ratio, redness, and scaling were scored to 0 point (none), 1 point (mild), 2 points (moderate), 3 points (severe) and 4 points (extremely severe), and were recorded daily during the course of the experiment. The results showed that the AR100 group, the AR111 group, and the AR112 group can effectively reduce the symptoms of scaling and redness in psoriasis, wherein the AR112 group has the best effect.

3. Measurements of Antibodies in the Blood

Figure 9:
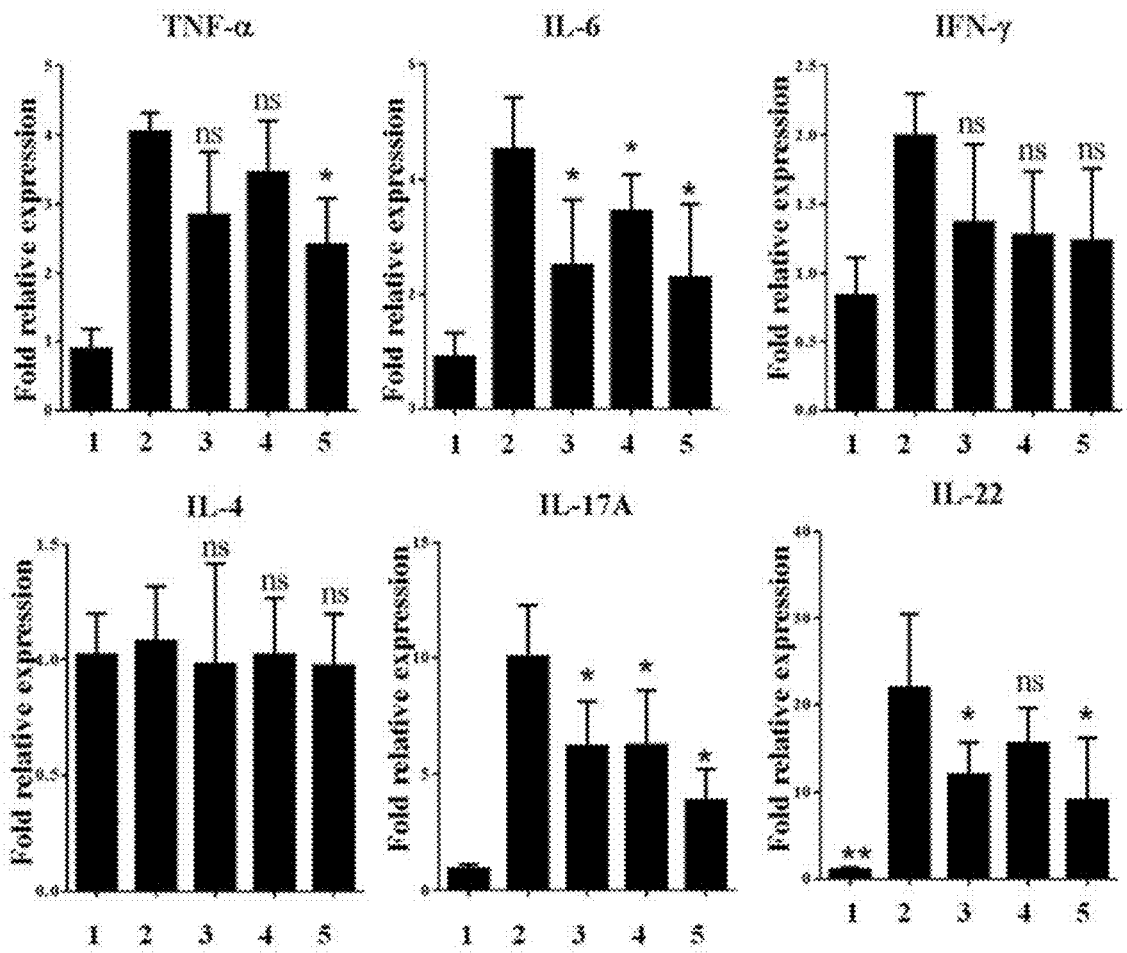
FIG. 9 provides the results of the real-time PCR in the psoriasis animal experiment (ns: $p>0.05$; *: $p<0.05$; **: $p<0.01$).

The cell factors of Th1 cells (IFN-γ), Th2 cells (IL-4), Th17 cells (IL-17A, IL-17F, IL-22), Th17 cells (IL-17A, IL-17F, IL-22), and inflammatory cytokines (TNF-α, IL-6) were analyzed by real-time PCR, so as to compare between IMQ/Base, IMQ/AR100, IMQ/AR111, and IMQ/AR112 on reducing psoriasis. As shown in FIG. 9, in the groups IMQ/AR100, the IMQ/AR111 and the IMQ/AR112, the mRNA expression of TNF-α, IL-6, IL-17 and IL-22 was reduced. It could be concluded that in the group IMQ/AR112 psoriasis could be improved by the composition containing AR001DS1 and AR001DS3.

4. Measurements of Splenomegaly

Figure 10:
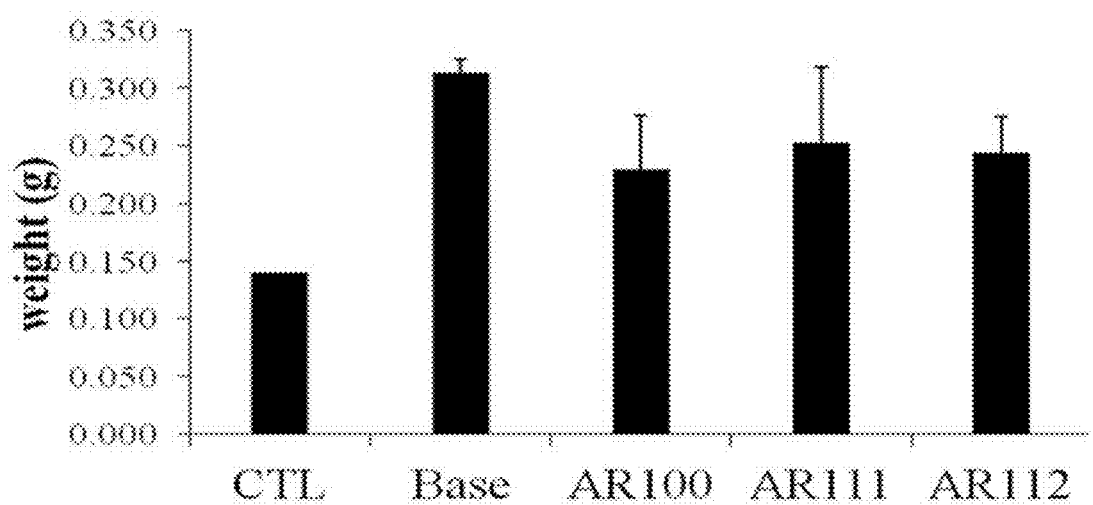
FIG. 10 provides the results of the spleen weights in the psoriasis animal experiment.

Under the IMQ induced psoriasis animals, splenomegaly, swelling of lymphoid organs, or swelling of lymphoid tissues were induced. The size and weight of the spleen were considered as inflammatory indexes in the experiment. As shown in FIG. 10, the efficacy in reducing inflammation under the IMQ induced psoriasis animals was found in terms of the mice spleen sizes and spleen weights as inflammatory indexes. In the groups IMQ/AR100, IMQ/AR111 and IMQ/AR112, the degree of splenomegaly in IMQ-induced mode were significantly reduced.

5. Measurements of Cytokine Expressions in Lymphocytes

Figure 11:
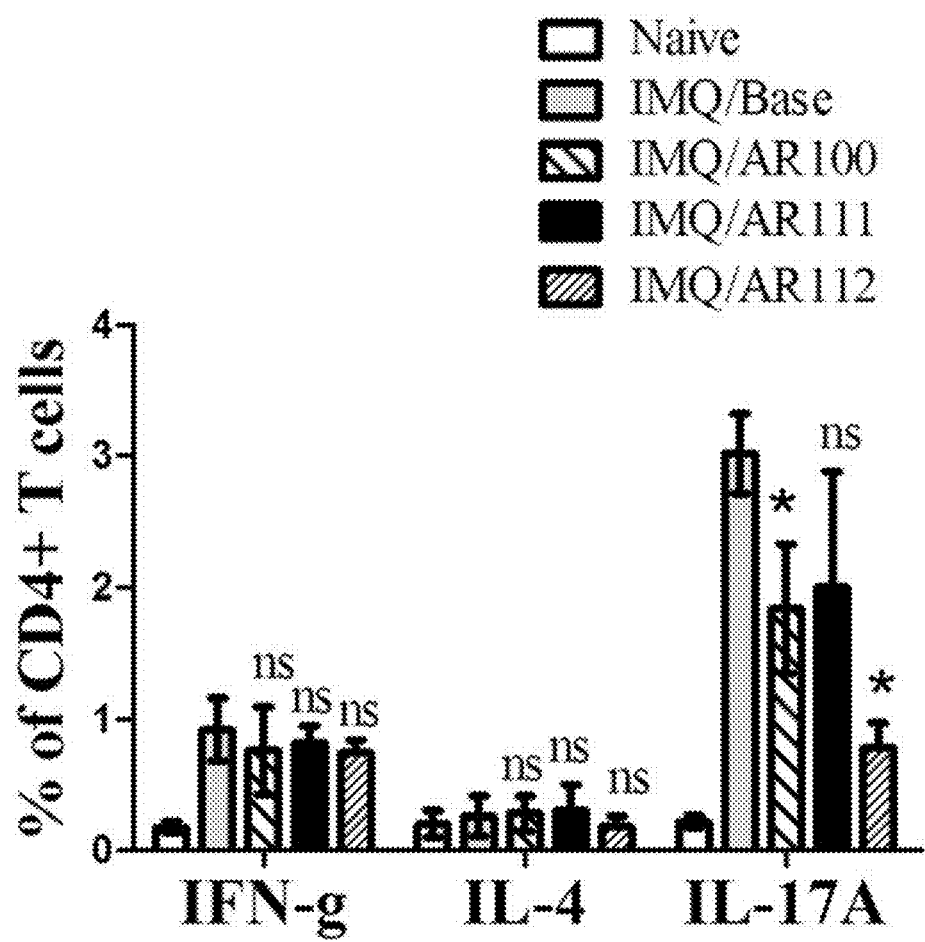
FIG. 11 is a chart showing the expression of the cellular factors in lymph cells in the psoriasis animal experiment (ns: $p>0.05$; *: $p<0.05$; *: $p<0.01$).

The expression of cytokines of Th1 cells (IFN-γ), Th2 cells (IL-1) in the lymphocytes of the groups IMQ/AR100, IMQ/AR111 and IMQ/AR112 were analyzed by flow cytometry. As shown in FIG. 11, it could be found that in the groups IMQ/AR100, IMQ/AR111, and IMQ/AR112, the expressions of Th17 cells were decreased, wherein the effects of the composition containing AR001DS1 and AR001DS2 and the composition containing AR001DS1 and AR001DS3 provided statistically significant effects.

Example 3 Autoimmune Hepatitis Animal Experiment

Autoimmune hepatitis (AIH) is a complex disease which is characterized by hepatocellular inflammation, necrosis, and a tendency to cirrhosis. The plant lectin concanavalin A (Con A)-induced acute hepatitis in BALB/c mice is a common animal model for AIH and we performed this model to evaluate the anti-hepatitis effects of AR001DS1. Dexamethasone (Dex), one of the steroids-based standard treatments of AIH, was used as a positive control.

To set up Con A-induced acute hepatitis in mice, we challenged the mice with 15 and 20 mg/kg Con A. Serum GOT and GPT levels were significantly increased in 15 mg/kg Con A-treated group when compared with sham controls (GOT: 1450±433 vs 140±23 U/L; GPT: 1437±398 vs 76±7 U/L). In regard to 20 mg/kg Con A-treated group, serum GOT levels were significantly increased (2249±549 vs 140±23 U/L) and serum GPT levels were increased without significance (2030±833 vs 76±7 U/L). No difference was observed between sham and naïve mice (GOT: 140±23 vs 135±20 U/L; GPT: 76±7 vs 83±2 U/L). Dex was used as a positive control in this study. The results showed Dex reduced the elevation of GOT induced by Con A (15 mg/kg Con A: 809±339 vs 1450±433 U/L; 20 mg/kg Con A: 1261±282 vs 2249±549 U/L). However, Dex only alleviated the levels of GPT induced by 15 mg/kg Con A (898±515 vs 1437±398 U/L) but not in 20 mg/kg Con A group (1940±403 vs 1437±398 U/L). In addition, body weight was decreased in all mice treated with Con A.

Next, histopathological analysis of liver tissues was conducted. Compared to sham controls, both 15 and 20 mg/kg Con A induced notable liver necrosis (score: 15 mg/kg Con A, 2.2±0.2 vs 0±0; 20 mg/kg Con A, 2.2±0.7 vs 0±0, $p<0.05$). Dex exhibited slight mitigation of tissue lesions after 15 mg/kg Con A induction (score 1.6±0.6 vs 2.2±0.2), but caused more severe lesions in 20 mg/kg Con A-challenged group (score 2.6±0.2 vs 2.2±0.2). Based on these results, we chose 15 mg/kg Con A for further study.

Figure 12:
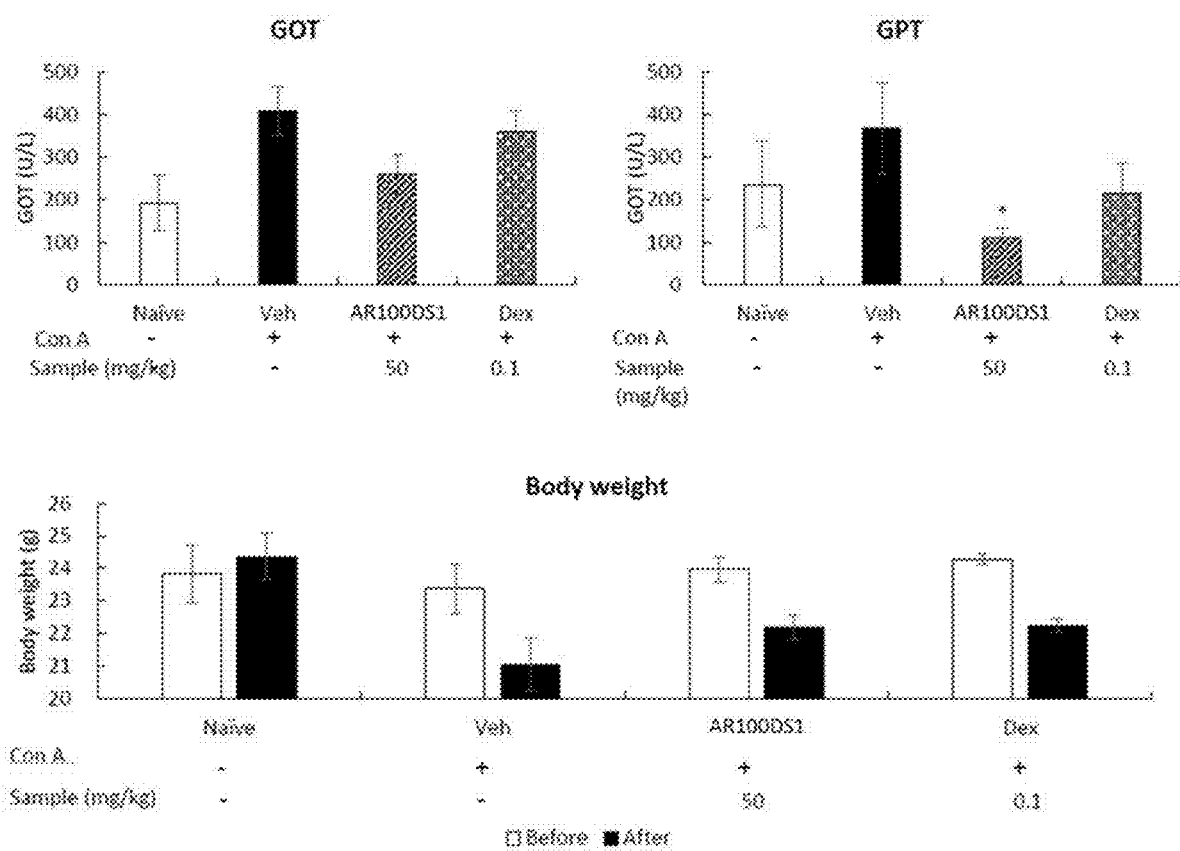
FIG. 12 shows effects of AR001DS1 on GOP, GPT and body weight. Data are presented as mean±SEM (n=9). *: p<0.05 versus Veh by the Student's t test. Veh, vehicle; Dex, dexamethasone.
Figure 13:
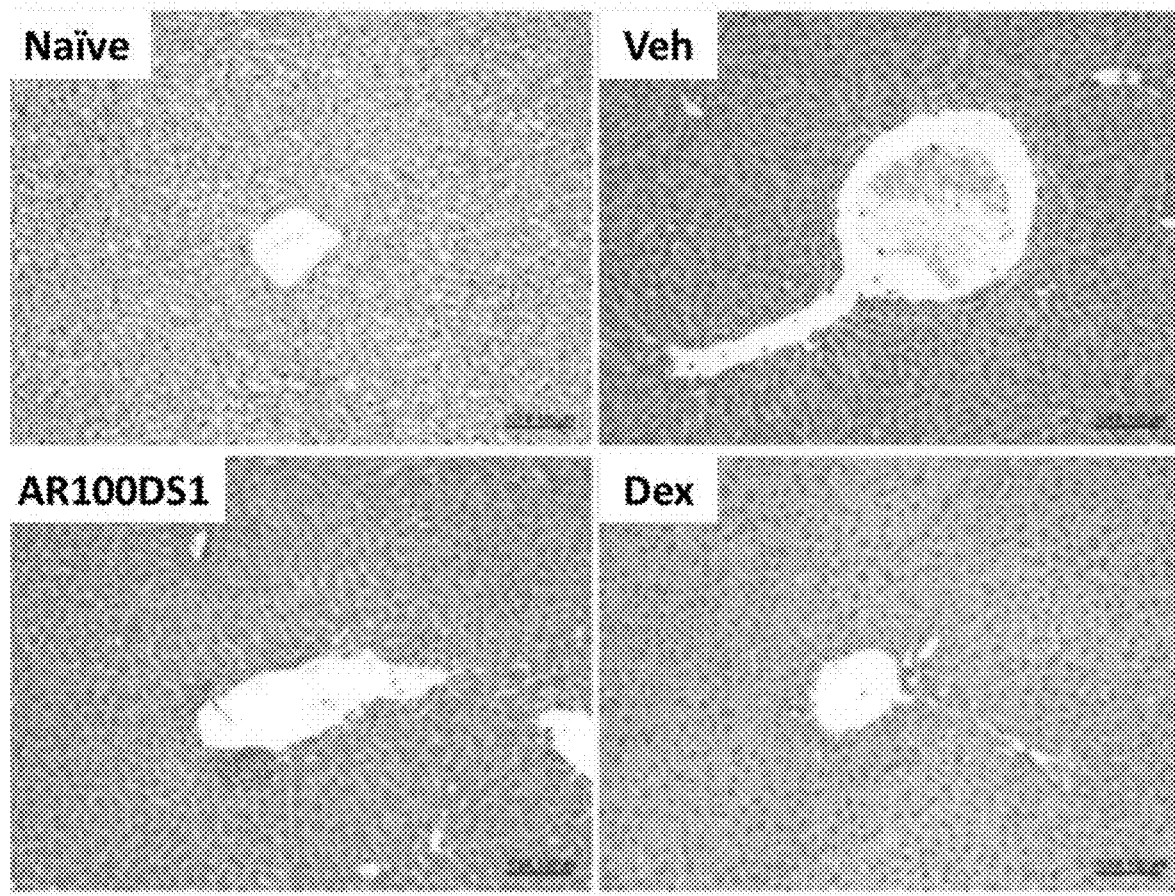
FIG. 13 shows effects of AR001DS1 on liver injury. Histopathological scores of necrosis are presented as mean±SEM (n=9). ***p<0.001 versus Veh by the Student's nest. Veh, vehicle; Dex, dexamethasone.
Figure 13:
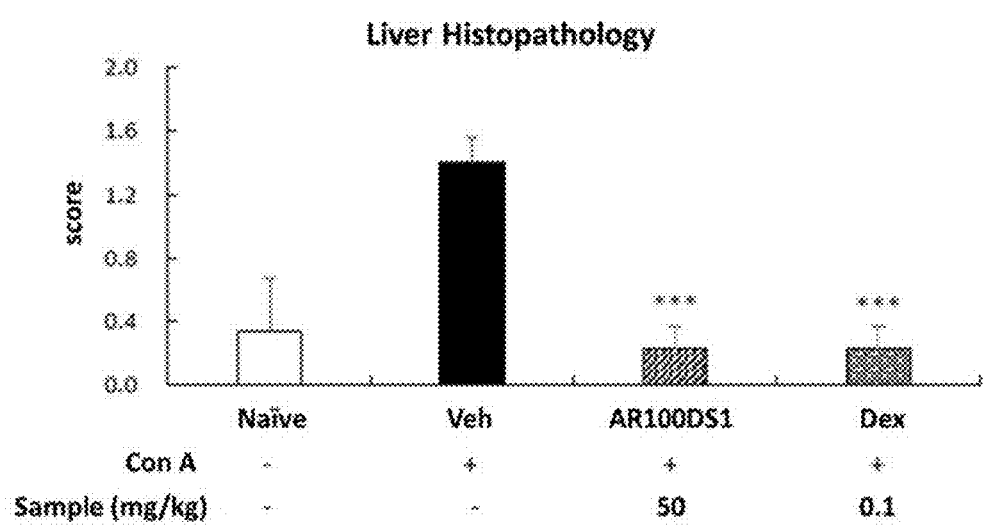

Lastly, AR100DS1 at 50 mg/kg significantly reduced GPT level that was increased by Con A (109±25 vs 368±107 U/L, $p<0.05$) and slightly improved elevation of GOT (261±45 vs 410±56 U/L) (FIG. 12). Also, histopathological analysis showed AR100DS1 ameliorated liver necrosis (score 0.2±0.2 vs 1.4±0.2, $p<0.05$) (FIG. 13).

Example 4 Antagonistic Effect of AR-100 on Inflammatory Signaling

Figure 14A:
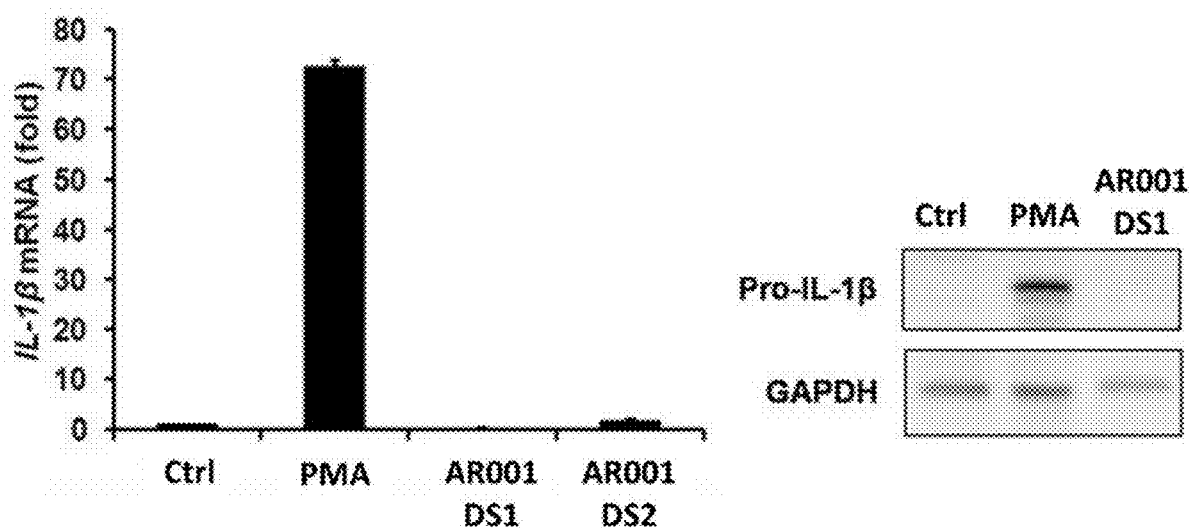
FIG. 14A shows that AR001DS1 or AR001DS2 pretreatment inhibits PMA-induced IL-1β expression in THP-1 cells. Q-PCR analysis (left) and immunoblotting (right) for IL-1β mRNA and protein expression in THP-1 cells pretreated with AR001DS1 or AR001DS2 for 0.5 h, followed by PMA induction for 48 h.
Figure 14B:
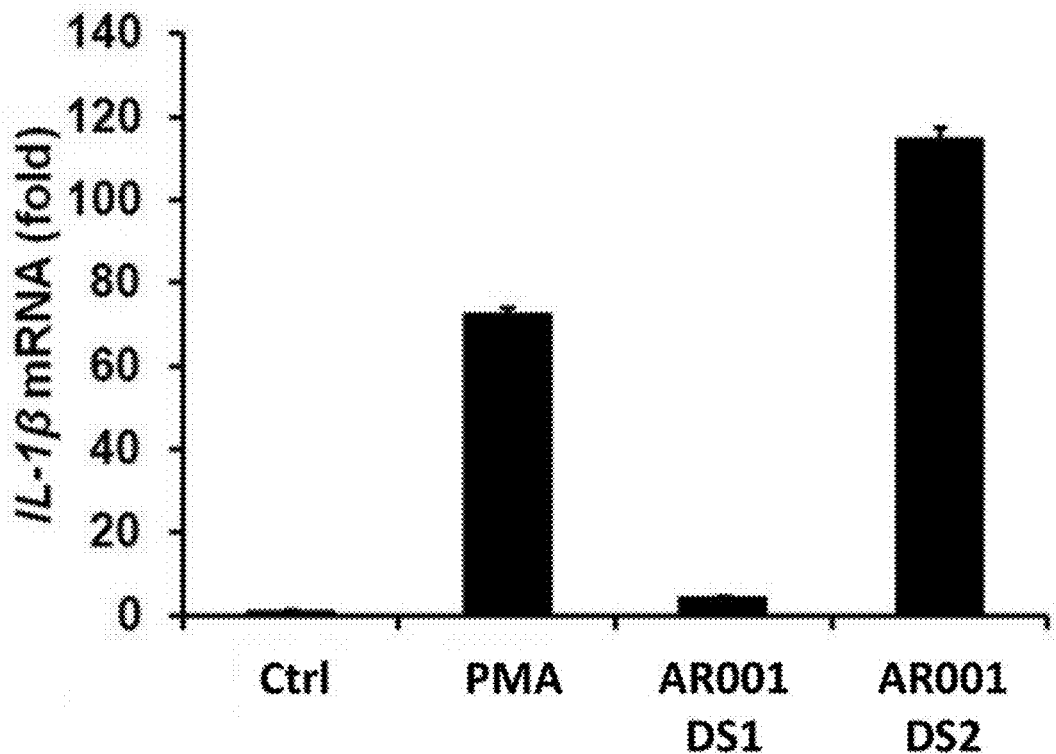
FIG. 14B shows that AR001DS1 treatment inhibits PMA-induced IL-1β expression in THP-1 cells. Q-PCR analysis for IL-1β mRNA expression in THP-1 cells stimulated with PMA for 24 h, followed by treatment with or without AR001DS1 or AR001DS2 for another 24 h.

Because AR001DS1 showed therapeutic effects on the animal model of gout arthritis, in which macrophage-released IL-1,6 played a critical inflammatory role, the effect of AR001DS1 on IL-1β-induction in phorbol-12-myristate-13-acetate (PMA)-activated THP-1 cells was tested. Because AR100 was composed of AR001DS1 and AR001DS2, THP-1 cells were independently pre-treated with the two components, followed by PMA activation. Q-PCR and immunoblotting showed that pretreatment of THP-1 cells with AR001DS1 or AR001DS2 blocked the expression of IL-1β (FIG. 14A). Intriguingly, activation of THP-1 cells with PMA followed by treatment of THP-1 cells with AR100DS1 still attenuated the expression of IL-1β while AR001DS2 did not suppressed PMA-induced IL1β (FIG. 14B). These data demonstrated that both AR001DS1 and AR001DS2 could suppress the initiation of inflammatory signaling in macrophage; moreover, AR001DS1 was capable of blocking inflammatory signaling in activated macrophage.

Example 5 Effects of Inflammatory Cytokines

Figure 15:
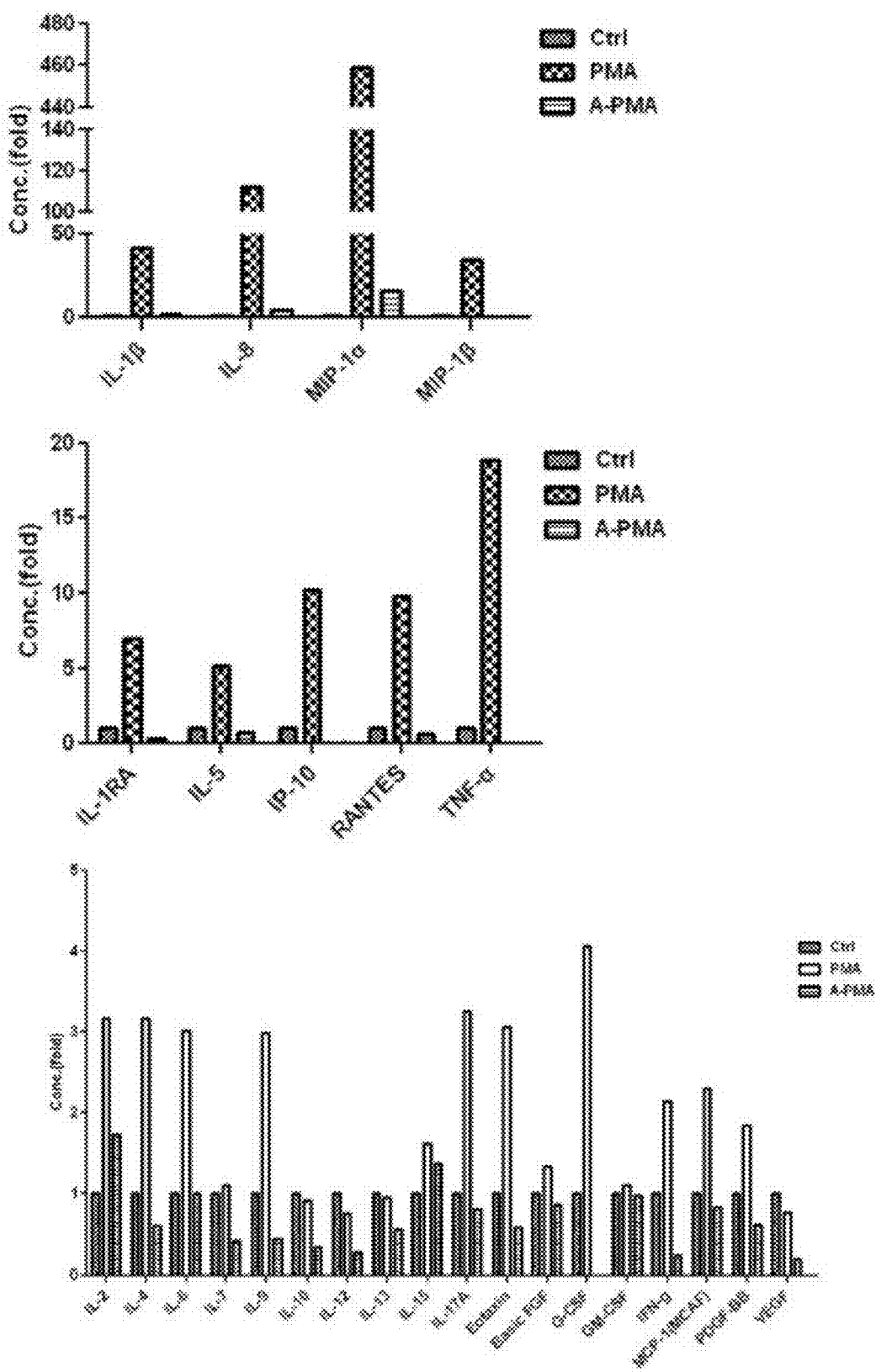
FIG. 15 shows the results of the bio-plex analysis using a human 27-plex cytokine assay to monitor the effect of AR100DS1 treatment (A-PMA) on PMA-induced cytokines; THP-1 cells were treated with AR001DS1 (10 µg/ml) for 0.5 hr, followed by PMA (10 ng/ml) treatment for 24 hr; AR001DS1 treated cells (A-PMA) together with PMA alone and untreated THP-1 (Ctrl) were subjected to Bio-plex analysis.

In addition to IL-1β, several cytokines participated in inflammatory responses. To identify cytokine networks affected by AR001DS1, we performed Bio-plex analysis to monitor the effect of AR001DS1 treatment on the expression of human 27 cytokines in PMA treated THP-1 cells. It was observed that PMA induced IL-1β whereas AR001DS1 treatment attenuated its expression. In addition, cytokines such as macrophage inflammatory protein (MIP)-α and -β were highly expressed during PMA-induced macrophage differentiation while AR001DS1 treatment blocked their expressions. As shown in FIG. 15, the induction of inflammatory cytokines such as IL-8, TNF-α and RANTES were also inhibited by AR001DS1 treatment. These data support that AR001DS1 could block the expression of inflammatory cytokines in macrophages.

Example 6

Considerable evidence supports the role of dendritic cells (DCs) in the pathogenesis of allergic diseases. Along with DCs, mast cells are one of the first immune cells to interact with allergens and other environmentally derived substances. Therefore, in this study we addressed the question of whether AR001DS1 suppresses the immune responses of mast cells and dendritic cells by utilizing RBL-2H3 (RBL) cell (mast cell line) and DCs from mice.

Figure 16:
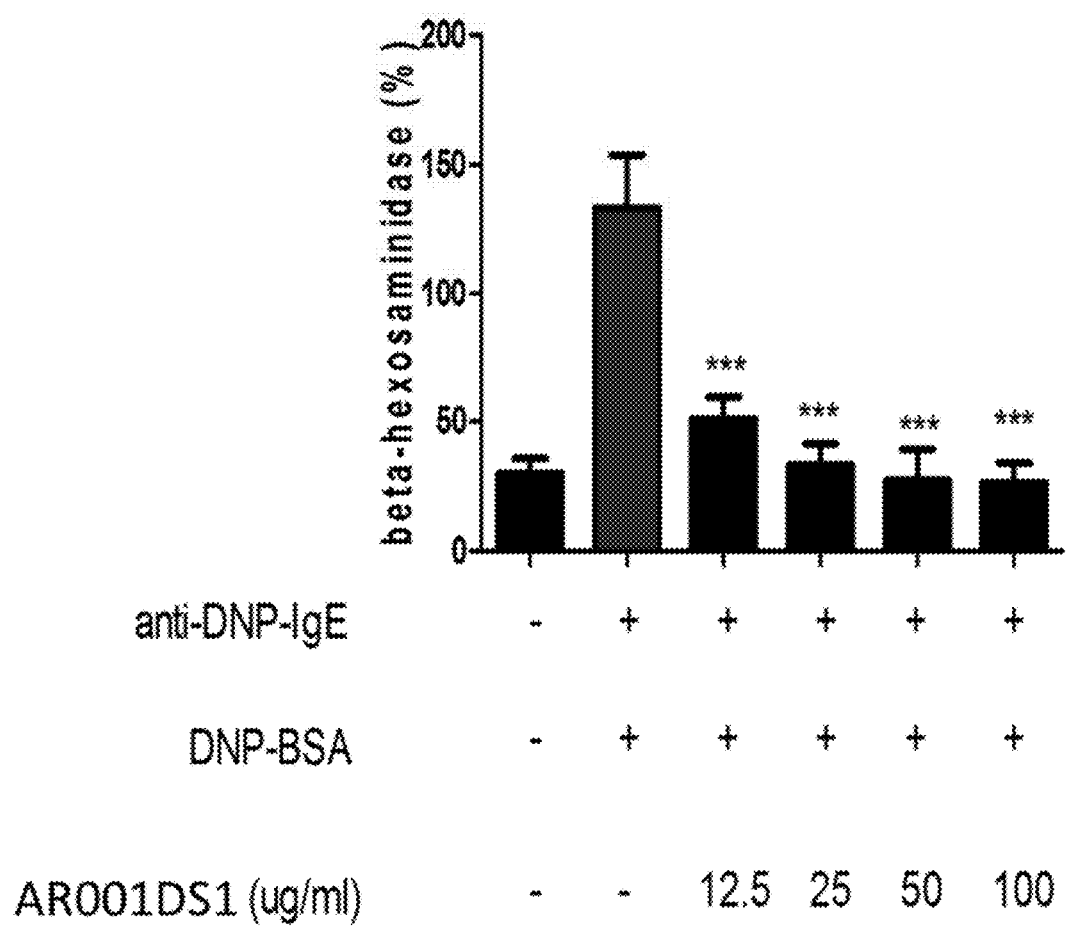
FIG. 16 provides the results that AR001DS1 could suppress mast cell degranulation in a dose-dependent manner. DNP, dinitrophenyl; DNP-BSA, dinitrophenyl-bovine serum albumin.

As shown in FIG. 16, antigen [DNP-bovine serum albumin (BSA)] stimulation caused a significant release of β-hexosaminidase from anti-dinitrophenyl (DNP) IgE-sensitized RBL cells. By contrast, secretion of β-hexosaminidase was significantly inhibited in AR001DS1-treated cells in a dose-dependent manner.

Figure 17:
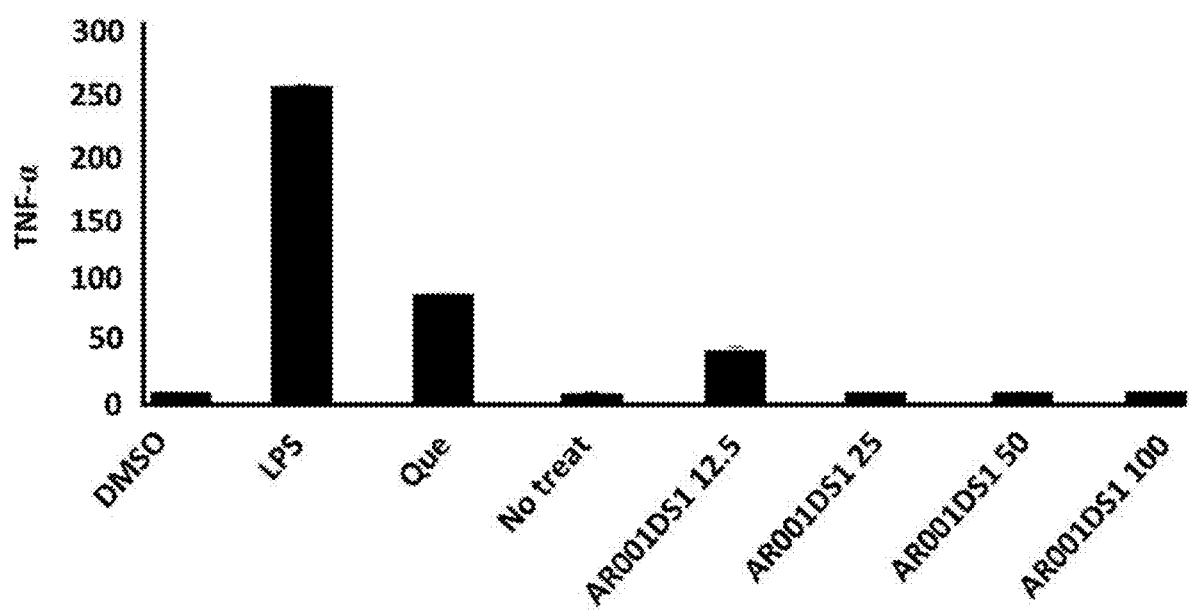
FIG. 17 provides the results that AR001DS1 could suppress TNF-α secretion by dendritic cells (DCs) in a dose-dependent manner. DMSO, DCs+0.1% DMSO; LPS: DCs+LPS+0.1% DMSO; Que: DCs+LPS+quercetin; No treat: DCs+culture medium; AR001DS1: DCs+LPS+AR001DS1.

Having observed that AR001DS1 could inhibit the secretion of β-hexosaminidase, we set out to determine whether AR001DS1 suppresses regulated exocytosis of other secretory granule cargo, such as TNF-α, in DCs. As shown in FIG. 17, lipopolysaccharide (LPS) stimulation induced a significant secretion of TNF-α, while quercetin, one of the best-known phytochemicals having anti-oxidant, anti-proliferative, and anti-inflammatory properties, effectively reduced the secretion of TNF-α in LPS-stimulated DCs. Surprisingly, AR001DS1 exhibited a better inhibitory effect on the secretion of TNF-α in LPS-stimulated DCs than quercetin.

While the present invention has been disclosed by way of preferred embodiments, it is not intended to limit the present invention. Any person of ordinary skill in the art may, without departing from the spirit and scope of the present invention, shall be allowed to perform modification and embellishment. Therefore, the scope of protection of the present invention shall be governed by which defined by the claims attached subsequently.

What is claimed is:

1. A method for treating an allergic disease which comprises administering to a subject in need thereof a therapeutically effective amount of a compound selected from the group consisting of ovatodiolide, 1'-acetoxychavicol acetate, and combination thereof.

2. The method of claim 1, wherein the compound is administered in a pharmaceutical composition.

3. The method of claim 1, wherein the compound is administered in a composition comprising an extract from an herb selected from the group consisting of *Anisomeles indica*, *Alpinia galangal*, *Zingiber zerumbet* and combination thereof.

4. The method of claim 1, wherein the allergic disease is selected from the group consisting of hay fever, food allergies, atopic dermatitis, asthma, psoriasis, contact dermatitis or eczema, autoimmune disease, osteoarthritis, allergy rhinitis, seborrheic dermatitis, psoriasis arthritis and poison ivy.

5. The method of claim 4, wherein the allergic disease is allergic dermatitis.

6. The method of claim 5, wherein the allergic dermatitis is atopic dermatitis.

7. The method of claim 5, wherein the allergic dermatitis is psoriasis.

8. The method of claim 4, wherein the allergic disease is autoimmune disease.

9. The method of claim 8, wherein the autoimmune disease is selected from the group consisting of autoimmune hepatitis, autoimmune pancreatitis, Sjogren' syndrome, ulcerative colitis, Crohn's disease, reflex sympathetic dystrophy, post myocardial infarction syndrome, rheumatoid rhinitis, multiple sclerosis, and cardiomyopathy.

10. The method of claim 8, wherein the autoimmune disease is autoimmune hepatitis.

\* \* \* \* \*